United States Patent

Siman et al.

[11] Patent Number: 5,387,199
[45] Date of Patent: Feb. 7, 1995

[54] POLYMER BLENDS FOR TORQUE TRANSMITTING CATHETERS

[75] Inventors: Jaime E. Siman, Santa Ana; Clement Lieber, Yorba Linda; Nancy Shadforth, Trabuco Canyon, all of Calif.

[73] Assignee: Baxter International Inc., Deerfield, Ill.

[21] Appl. No.: 204,796

[22] Filed: Mar. 2, 1994

Related U.S. Application Data

[63] Continuation of Ser. No. 840,427, Feb. 24, 1992, abandoned.

[51] Int. Cl.⁶ .............................................. A61M 25/00
[52] U.S. Cl. .................................. 604/282; 604/264; 424/78.1
[58] Field of Search ...................... 604/264–266, 604/280, 282, 272, 93, 96; 623/1, 11, 12; 424/78.1

[56] References Cited

U.S. PATENT DOCUMENTS

| | | | |
|---|---|---|---|
| 3,962,519 | 6/1976 | Rüsch et al. | 604/265 |
| 4,381,380 | 4/1983 | LeVeen et al. | 604/265 |
| 4,753,765 | 6/1988 | Pande | 604/264 |
| 4,790,831 | 12/1988 | Skribiski | 604/204 |
| 4,867,968 | 9/1989 | Allen | 604/264 |
| 4,886,506 | 12/1989 | Lougren | 604/96 |
| 4,898,591 | 2/1990 | Jang et al. | 604/264 |
| 5,019,096 | 5/1991 | Fox, Jr. et al. | 604/265 |
| 5,078,700 | 1/1992 | Lambert et al. | 604/264 |
| 5,116,652 | 5/1992 | Alzner | 604/264 |
| 5,156,785 | 10/1992 | Zdrahala | 604/264 |

FOREIGN PATENT DOCUMENTS

| | | |
|---|---|---|
| 0017111 | 3/1980 | European Pat. Off. |
| 0422693A2 | 6/1986 | European Pat. Off. |

OTHER PUBLICATIONS

Results of Data Base Search relating to high torque catheters.
Abstract of JP 50079559, Database WPI, Derwent Publications Ltd., AN 76-11880X.

*Primary Examiner*—C. Fred Rosenbaum
*Assistant Examiner*—Chalin Smith
*Attorney, Agent, or Firm*—Bruce M. Canter; Janis C. Henry

[57] ABSTRACT

Polymer blends having improved torque transmitting properties are disclosed. The polymer blends include polyetherurethane and a concentration of polyetherester sufficient to provide the polymer blend with a 37° C. dynamic torque value greater than 40% of the polymer blend's 25° C. dynamic torque value. The polymer blend can be thermally processed to form small diameter tubing suitable for general purpose catheters requiring both a high degree of maneuverability and sufficient resiliency to avoid tissue perforation.

22 Claims, No Drawings

POLYMER BLENDS FOR TORQUE TRANSMITTING CATHETERS

RELATED CASES

This application is a continuation of co-pending U.S. application Ser. No. 07/840,427, filed on Feb. 24, 1992 now abandoned.

BACKGROUND OF THE INVENTION

1. Field of the Invention

The present invention generally relates to thermoplastic polymers utilized in small diameter tubing for catheter bodies. More particularly, the present invention relates to polymer blends useful for forming catheter bodies having improved torque transmitting properties for easy maneuverability through tortuous body pathways yet having sufficient compliance to avoid tissue perforation.

2. Description of Related Art

Thermoplastic polymers, copolymers, and polymer blends have been used extensively in the fabrication of medical devices, including a wide range of long term and short term implant devices. Many polymers and polymer blends used in medical devices have specific physical and chemical properties which make them particularly suitable for in vivo applications. Preferred chemical, physical and thermomechanical properties depend upon the specific function, the type of tissue, cells or fluids contacting the medical device and the acceptable or desired manufacturing processes. Major considerations in choosing polymers for medical devices include the chemical stability of the polymer, particularly hydrolytic stability, the toxicity of the polymer, and the degree of interaction between tissue or blood and the polymer. Additionally, the polymer or polymer blend should meet all the physical demands relating to the function of the medical device including strength, compliance, stiffness, torque and rebound properties. Also, it should be compatible with and contribute to stable manufacturing and assembly processes.

Catheters represent a particularly large class of medical devices used for a variety of in vivo applications. Typically catheter bodies are formed of one type of polymer, but more than one type can be incorporated into the catheter body in order to provide a device which meets the catheter's physical and chemical requirements. One type of catheter which is widely utilized in a variety of procedures is physically designed to be maneuvered through tortuous fluid pathways within a body to a preselected site. Once maneuvered into place the catheter and its components are used to assist in the performance of a variety of monitoring functions such as cardiac output monitoring, pulmonary artery pressure monitoring and blood chemistry analyses. The catheter is frequently allowed to remain for a period of several days inside the body while liquids and medicaments are infused through its lumens and into the fluid pathway.

In order to safely maneuver the catheter into place, the material used to fabricate the catheter body should have sufficient rebound and low enough bend stiffness to avoid perforating or otherwise harming vessel endothelial tissue. That is, the material should have such combinations of mechanical properties as to allow the catheter to move away from the vessel wall without damaging it, should it inadvertently collide with the wall. At the same time, the material should have good torque transmitting properties to provide catheter maneuverability.

Torque transmitting properties are particularly important when a catheter is being introduced in the heart via the inferior vena cava. When introduced into the right heart, the catheter distal tip must first turn in one direction to pass through the tricuspid valve and then do an abrupt turn in order to traverse the right ventricle and enter the pulmonary artery. During this process, the proximal end of the catheter is frequently subjected to a constant torque in order to maneuver the catheter distal tip to the selected site.

When subjected to constant torque at the proximal end, the distal end of catheters fabricated of some materials will seem to be stuck at one point and then rapidly "whip" to another position. This "whipping" action can cause serious tissue damage or tissue perforation. Hence, optimum catheter materials should be designed to provide enough maneuverability, yet reduced chance of harmful "whipping".

Catheter torque transmissibility should be maintained at both ambient temperatures and body temperature because during the insertion process a large part of the catheter is external to the body and remains at room temperature. At the same time, the distal end of the catheter reaches body temperature and if the torque decreases substantially at the elevated temperature, the catheter maneuverability will be unacceptable.

Plasticized polyvinylchloride has been used widely to form a number of types of general purpose catheters. The torque transmitting properties of this polymer are good at room temperature. Plasticized polyvinylchlorides however, exhibits a significant decrease in torque at body temperatures, when ideally the torque should be still high enough to facilitate maneuverability once the portion of the catheter in the body warms to body temperature. Thus, polyvinylchloride catheters fall short of having ideal torque transmitting properties.

In an attempt to improve the maneuverability of these catheters, some manufacturers have incorporated braids of suitable materials into the walls of extruded catheters. These braids have the effect of increasing the torque transmitting characteristics without severely compromising the flexibility of the catheter.

A major disadvantage associated with using braids is that the functional demands of these catheters have increased to the point that 7F catheters with 5 lumens are common. These high performance catheters are frequently coated with a heparin complex so that they can remain within a blood vessel for several days without causing excessive platelet formation. During this time all lumens may be utilized to perform a variety of functions. In order to accommodate 5 lumens within a single catheter, the catheter walls and the lumen walls must be very thin which necessarily leaves little volume for incorporating braids within the walls.

Another disadvantage associated with polyvinylchloride catheters involves the public concern, particularly in European countries, regarding the use of this polymer. This concern relates to environmental disposal problems associated with PVC. Additionally, polyvinylchloride catheters require substantial levels of plasticizer in their material formulation and the use of these plasticizers present various challenges. The plasticizers tend to migrate to the surface, becoming a potential problem to neighbor components which may absorb them. Also, as the plasticizer content changes the thermomechanical properties of the part change. This limits the shelf life of the product.

During the past decade researchers have learned a great deal about the interaction of materials with blood and tissue. Studies have indicated that certain polymers are much more compatible with blood and tissue in that they cause less platelet formation and less severe inflammatory response when implanted in living organisms. While, polyvinylchloride catheters have been used extensively by medical professionals, polyvinylchloride is not known to have exceptional biocompatibility. On the other hand, polyurethanes have recently gained recognition for their biological compatibility.

Accordingly, it is an objective of the present invention to provide a polymeric composition which can be used to fabricate catheters having good torque transmission properties at ambient temperatures and at body temperatures, and having sufficient softness and flexibility to avoid tissue trauma.

It is additionally an objective of the present invention to provide a polymeric composition having improved blood and tissue compatibility.

It is another objective of the present invention to provide a polymeric composition which is homogeneous at its melt temperature and easily processed into small diameter tubing.

It is another objective of the present invention to provide a polymeric composition for fabricating into catheters having surfaces which will accept coatings of heparin complexes.

SUMMARY OF THE INVENTION

The present invention accomplishes the above described objectives and others by providing a polymeric composition which includes a thermoplastic polymer blend of two different yet compatible types of copolymers, each of which has a recognized degree of biocompatibility. Advantageously, the polymer blend can be thermally processed to form small diameter tubing having improved torque transmitting properties at both 25° C. and 37° C. Additionally, the compositions of the present invention have utility in the fabrication of small diameter tubing with exceptional mechanical properties, including resiliency. Accordingly, the compositions of the present invention are suitable for use in general purpose catheters requiring a high degree of maneuverability.

In its broadest aspect, the compositions of the present invention are thermoplastic homogeneous polymer blends of polyetherurethane and polyetherester. In order to enhance their 37° C. torque characteristics, the polymer blends of the present invention have a concentration of polyetherester sufficient to provide the polymer blend with a 37° C. dynamic torque value greater than 40% of their 25° C. dynamic torque value. The presence of the polyetherester in the polymer blends also enhances the rebound properties without detriment to the blend minimum bend stiffness required for ease of passage through the introducer, and to provide materials suitable for catheter fabrication.

Exemplary embodiments of the present invention preferably include three polyetherurethanes having different hardness values ranging in Shore hardness from about 40D to about 75D. These polyetherurethanes differ in the molecular weights or chain lengths of the ether portions of the copolymers. Additionally, these polyetherurethanes are recognized within the medical community to have tissue and blood compatibility properties which are superior to other organic based polymers.

In accordance with the present invention, exemplary embodiments further include a radiopaque filler material such as barium sulfate. When incorporated into the polymer blend the radiopaque filler allows devices fabricated from the polymer blend to be visualized using x-ray fluoroscopic methods. Thus, catheters formed from the compositions of the present invention can be inserted into body pathways while maintaining full visualization of the catheter movement with x-ray fluoroscopy.

In addition to providing polymer blends with advantageous torque transmitting properties, the compositions of the present invention form devices having surfaces which are easily coated with heparin complexes using conventional coating techniques. Moreover, these devices form stable and strong bonds with many organic adhesives, thus allowing easy fabrication of devices having attachments such as balloons.

A particularly important benefit associated with the polymer blends of the present invention is that they yield reproducible, stable and capable extrusion processes. The polyetherurethane and polyetherester polymer blends of the present invention can be extruded into high quality, consistent and uniform tubing of small diameter. An optimum and stable melt temperature, pressure and corresponding extrusion profile are easily determined with suitable precision extrusion equipment.

Further objects, features and advantages of the polymer blend compositions of the present invention, as well as a better understanding thereof, will be afforded to those skilled in the art from a consideration of the following detailed explanation of preferred exemplary embodiments.

DETAILED DESCRIPTION OF EXEMPLARY EMBODIMENTS

The polymer blend compositions of the present invention are intended for use in fabricating small diameter tubing having excellent maneuverability and improved torque transmission requirements, yet exhibiting relatively low but sufficient bend stiffness value. Because the compositions of the present invention have advantageous torque and rebound properties at both 25° C. and 37° C., as well as a recognized biocompatibility, they are particularly suitable for fabricating tubing for catheter bodies requiring torque transmitting properties at ambient temperatures and physiological temperatures. Exemplary catheters include pulmonary artery flow-directed thermodilution catheters. Those skilled in the art will appreciate, however, that the polymer blend compositions of the present invention have utility in any application requiring materials having torque transmissibility and relatively low bend stiffness at ambient and elevated temperatures.

The present invention is based upon the discovery that polyetherurethane, highly recognized for its biocompatibility, can be utilized to fabricate high torque catheters when used in combination with polyetherester. Polyetherurethanes alone have little utility in torque catheter applications because urethanes generally lose over 60% of their torque properties when exposed to physiological temperatures. Compensating for the loss of these torque properties by using a very high Shore hardness polyurethane is not a workable approach because high Shore hardness polyetherurethanes are too stiff at room temperature. Thus catheters prepared from these polyurethanes have a high tissue perforation risk during their insertion into the body.

diisocyanate (MDI) and have the following general structure:

(CH$_2$)$_4$—OC—N—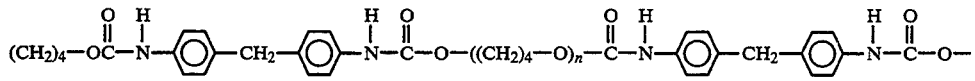—N—C—O—((CH$_2$)$_4$—O)$_n$—C—N—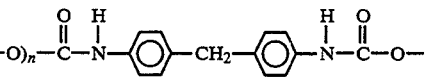—N—C—O—

This discovery has lead to the development of polymer blends having physical properties which are far more suitable for catheter fabrication than either of the single polymers. Thus, the polymer blends of the present invention combine the torque properties of different polymers and take advantage of their performance at different temperatures, specifically at 25° C. and 37° C. to provide compositions having improved torque transmissibility at ambient and physiological temperatures.

At the same time, the compositions of the present invention have physical properties which make their use safe in terms of their ability to avoid perforating or traumatizing tissue, at ambient temperatures as well as physiological temperatures. Moreover, unlike prior art polymeric compositions used to fabricate many catheters, the polymer blends of the present invention do not include undesirable plasticizers or chlorinated polymers and each of the polymers included in the polymer blend is accepted in the medical community for in vivo use.

Broadly, the compositions of the present invention are polymer blends of polyetherurethane and polyetherester in which the polymer blend has a polyetherester concentration sufficient to provide the polymer blend with a 37° C. dynamic torque value greater than 40% of the 25° C. dynamic torque value of the polymer blend. Exemplary embodiments of the present invention incorporate at least about 5 w/w% (weight percent) polyetherester in order to maintain the desired torque values at 37° C. Preferably, the polymer blends of the present invention further include biologically acceptable radiopaque filler material for visualization of the polymer blend under x-ray fluoroscopy, and coloring agents such as pigments or TiO$_2$.

More particularly, exemplary polymer blends of the present invention include from about 25 w/w% to about 75 w/w% polyetherurethane, from about 5 w/w% to about 45 w/w% polyetherester, from about 15 w/w% to about 30 w/w% filler of radiopaque material, and about 1 w/w% TiO$_2$.

Polyetherurethanes suitable for use in the polymer blends of the present invention include compounds having the following general structure:

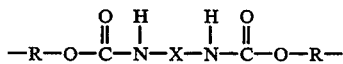

wherein R is a divalent polyether radical, and X is a divalent organic radical. Generally, these polyetherurethanes are the reaction product of polyether glycols of varying molecular weights and isocyante terminated organic compounds. The polyether glycols are typically polyethylene oxide, polypropylene oxide, or polytetramethylene oxide of various molecular weights. The isocyanate terminated organic compounds range in structure from substituted aromatic diisocyanates to small molecular weight alkyl diisocyantes.

Preferred exemplary embodiments of the present invention include polyetherurethanes of polytetramethylene oxide (PTMG) and diphenylmethane-4,4'-diisocyanate (MDI) and have the following general structure:

wherein n>1. MDI and PTMG based polyetherurethanes having a number of different Shore hardness values are available commercially from DOW Chemical under the tradename PELLETHANE. PELLETHANES are recognized within the medical community as having a relatively high tissue and blood compatibility and are used in a number of medically related applications. Moreover, they can be extruded or heat formed into a variety of shapes with ease.

Those skilled in the art will appreciate that by varying the molecular weight of the polyether portion of polyetherurethanes, the Shore hardness can be controlled. Thus, PELLETHANES having relatively long chain polytetramethylene ether portions have lower Shore hardness values than similar polyetherurethanes having shorter polytetramethylene ether portions. The Shore hardness of PELLETHANE polyetherurethanes range from a relatively soft. 80 A (about 40 D) to a harder 75 D.

Polyetheresters suitable for use in the polymer blends of the present invention include compounds having the following general structure:

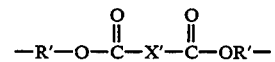

wherein R' is a divalent polyether radical, and X' is a divalent organic radical. Thus, polyetheresters include a polyether portion and an organic ester portion. Like the ether portions of the polyetherurethanes, the polyether glycols are typically polyethylene oxide, polypropylene oxide, or polytetramethylene oxides. Similarly, the organic ester portion ranges in structure from substituted aromatics to small molecular weight alkyls.

Preferred exemplary embodiments of the present invention include polyetheresters of polytetramethylene oxide (PTMG) and terephthalic acid esters and have the following general structure:

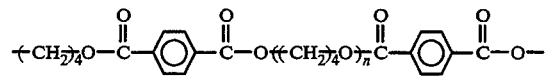

wherein n>1. Polyetheresters having the above-described general structure are available from DuPont Polymers of Wilmington, DE under the tradename HYTREL. HYTREL is called by the CAS nomenclature to be a 1,4-benzenedicarboxylic acid, dimethylester, polymer with 1,4-butanediol and alpha-hydro-omega-hydroxypoly(oxy-1,4butanediyl).

Suitable fillers of biologically acceptable radiopaque material include barium sulfate (BaSO$_4$) powder and bismuth subcarbonate powder. These filler materials have a history of medical use and are commonly incorporated into polymeric formulations for the purpose of producing radiopaque catheter bodies. Due to its cost, ease in handling and processing BaSO$_4$ is a preferred radiopaque filler material.

The polyetherurethanes utilized in the compositions of the present invention exhibit substantial changes in their mechanical properties at physiological temperatures (37° C.). At ambient conditions, polyetherurethanes exhibit desirable torque-transmissibility characteristics. However, once exposed to physiological temperatures, polyetherurethanes do not have favorable torque properties, maintaining less than 40%, of their ambient temperature torque value. Furthermore, polyetherurethanes are highly moisture sensitive, demanding optimum drying for quality extrusion processing. These polymers also exhibits lower than desired resiliency.

Polyetheresters, on the other hand, do not exhibit significant changes in mechanical properties between ambient and physiological temperatures. Thus, the torque transmissibility of HYTREL does not substantially decrease at physiological temperatures. Disadvantageously, polyetheresters, such as the HYTREL polymers, have very high rebound properties. HYTREL is "bouncy", and catheters fabricated from only these polyetheresters have too much dangerous "whipping". But in combination with the polyetherurethane, polyetheresters offer balanced rebound properties. Thus, in addition to contributing to improved torque transmitting properties at 37° C, polyetheresters are instrumental in providing the polymer blend composition of the present invention with advantageous and optimized rebound properties at both ambient temperatures and at 37° C. The combined properties make the compositions of the present invention suitable for forming catheters having little tendency to perforate or otherwise traumatize tissue, while providing excellent insertion and maneuverability properties.

From the above discussion it can be appreciated that by balancing and controlling the relative concentrations of polyetherurethanes and polyetheresters the polymer blend compositions of the present invention can be formulated to provide improved torque transmissibility at ambient and physiological temperatures while simultaneously optimizing rebound properties, ambient temperature column strength for ease of insertion, and extrusion processability.

Additionally, in accordance with the teachings of the present invention, to more advantageously balance the torque, rebound and bend stiffness properties at ambient and physiological temperatures, the polymer blends of the present invention preferably include more than one polyetherurethane of different Shore hardnesses and flexural modulus. As mentioned above, PELLE-THANES, in particular, are available in a range of Shore hardnesses. Thus, it is possible to take advantage of these different hardnesses and modulus to formulate polymer blends with a variety of especially advantageous properties.

Using a polyurethane with sufficiently high Shore hardness (e g D75 and D65) provides material suitable for catheters having good ambient temperature column strength and stiffness. This allows the catheter to enter through the introducer into the body vessels with ease and without kinking. The decrease in torque value at body temperature caused by polyetherurethane is balanced by the lower Shore hardness polyetherester copolymer (e.g. Shore D55 ), which additionally retains a higher degree of torque at body temperature. The low Shore hardness polyetherester copolymer contributes to the polymer blends low perforation potential in the body.

Exemplary embodiments of the present invention are illustrated in Table I. A polymer blend of polyetherurethanes, polyetherester, $BaSO_4$, and $TiO_2$ having the formulation A detailed in Table I has a dynamic torque of 19 gm-cm at 25° C. at 18° rotation and a dynamic torque of 10 gm-cm at 37° at 18° rotation, both samples (25° C. and 37° C.) having the same tube cross-section, and tested at same conditions (frequency of rotation, etc.). On the other hand, a polymer blend of polyetherurethanes, polyetherester, $TiO_2$, and $BaSO_4$ having the formulation B detailed in Table I has a dynamic torque of about 11 gm-cm at 25° C. at 15° rotation, and a dynamic torque of 7 gm-cm at 37° at 15° rotation, determined from samples of similar cross-sectional dimensions at the same frequency of rotation. The torque measurements associated with both formulation A and formulation B are suitable for polymer blends utilized to formulate torque catheter bodies. The performance of each blend can be compared by examining the relative change in torque between ambient and body temperature. Each formulation provides a 37° C. torque value which is greater than 50% of its 25° C. torque value, thus maintaining catheter maneuverability at physiological temperatures.

Formulation B, which additionally includes a softer polyetherurethane, provides good torque retention with somewhat lower, yet enough, torque at both temperatures. The softer polyetherurethane also contributes to an overall balance in the rebound properties which further guards against "whipping" and tissue perforation problems. The preferred balance in rebound properties associated with Formulation B was empirically determined by clinical professionals handling catheters formed from formulation B.

TABLE I

| POLYMER | FORMULATION A w/w % | FORMULATION B w/w % |
| --- | --- | --- |
| PELLETHANE 2363-65D | 0 | 45 |
| PELLETHANE 2363-75D | 16.0 | 7.2 |
| PELLETHANE 2363-80A | 12.9 | 12.4 |
| HYTREL 5526 | 39.9 | 6.4 |
| $BaSO_4$ | 30 | 28 |
| $TiO_2$ | 0.8 | 1 |
| PIGMENT | 0.4 | |

The polymer blends of the present invention can be prepared using conventional compounding techniques. Commonly, compounding involves properly weighing and adding each of the formulation components in a blender to homogenize the mixture and then drying the blend in a vacuum oven, typically at 212° F. Finally, the blend is pelletized in a single screw or a twin screw extruder. A twin screw extruder is preferred because they provide superior sheer and mixing conditions. Typically, the polyetherurethane and polyetheresters are obtained in pellet form from the manufactures and are properly dried to a minimum moisture level prior to pelletizing them in the extruder. Maximum homogenicity is obtained when the polymers in pellet form are ground into a powder (35 mesh) before they are blended, dried and pelletized. This is specially true when ingredients such as barium sulfate are in powder form.

The radiopaque filler materials and pigment or $TiO_2$ can be precompounded with one of the polymers to make a concentrate in pellet form. This is recommended when the other polymers are added in pellet form because the powders potentially gravimetrically separate from the polymer pellets in the extruder hopper and cause variations in along the extrusion run. After the formulation components are added and mixed to a homogeneous blend, the blended components are extruded into pellets for use in a final fabrication step. The pellets should be void free and smooth.

A particularly advantageous feature of the present invention relates to the high reproducibility associated with compounding and extruding the polymer blends of the present invention. The polymers used in this invention have similar and compatible processing melt temperatures. This is important to obtain an homogeneous and consistent melt. Consequently, the compositions of the present invention provide extrusion grade polymer blends which form high quality extruded product in a highly reliable and reproducible manner. Furthermore, small diameter tubing, such as that used in catheters, can be extruded in bulk quantities, with consistently high quality. The consistently high quality includes uniform wall thickness, lumen shape and size, and overall dimensions.

Thus, catheters useful for accessing body cavities during therapeutic and diagnostic medical procedures, and especially catheters requiring a high level of maneuverability, are advantageously formed from the polymer blends of the present invention. Accordingly, it is contemplated to be within the scope of the present invention to provide catheters which include an elongated tubular member having at least one lumen, and formed of a heat extruded homogeneous polymer blend of polyetherurethane and polyetherester. The catheters of the present invention can be multi-lumen catheters intended for use in accessing sites within the body for therapeutic and diagnostic purposes. These catheters include, but are not restricted to, pulmonary artery flow-directed thermodilution catheters.

In addition to being highly maneuverable and presenting little risk of perforating or traumatizing tissue, the catheters of the present invention have advantages associated with the actual catheter construction. For example, the polymer blends of the present invention are compatible with heparin complex solutions utilized to coat certain catheters for antithrombogenic properties. Furthermore, heparin complexes form uniform films on the catheter surface and the films are not easily removed from the surface as the result of incidental handling. Importantly, the heparin retains a high antithrombogenic activity subsequent to its deposit on the surface of the catheters of the present invention. In contrast to catheters fabricated of polyvinylchloride, the catheters of the present invention do not contain plasticizers which can migrate to the surface and into other components of the catheter like the balloon.

Another advantage associated with the construction of the catheters of the present invention is the ease with which balloons and other components can be made to adhere to the catheter body. Balloons can be secured to the catheters of the present invention using adhesives without the necessity of winding. Suitable adhesives include acrylates, cyanoacrylates, epoxies, and urethanes. These adhesion properties are attributed to the strong bonds formed by the polymer blends and a wide variety of adhesives.

Another feature of the polymer blends of the present invention is the wide range of techniques available for sterilizing catheters fabricated of the polymer blend. The polyetherurethane and polyetherester polymer blends can be exposed to sterilizing doses of ionizing radiation and they can be ethylene oxide sterilized utilizing common temperature and pressure cycles without adverse effects to the strength and the function of the blends.

Further, in connection with the particular ease with which the polymer blends of the present invention are formulated and extruded, catheters prepared from the polymer blends of the present invention have tips which are reliably and quickly heat formed with very high yields. These heat formed tips so produced are smooth and nontraumatic.

Some of above-described many features and advantages associated with the polyetherurethane and polyetherester blends of the present invention and catheters fabricated thereof as well as exemplary polymer blends and comparative formulations are further illustrated in the following nonlimiting examples.

EXAMPLE 1

In order to evaluate the torque properties of exemplary polymer blends of the present invention relative to formulations comprising polyurethanes, polyetherurethane, and polyvinylchloride, a number of polymer formulations were compounded and extruded into tubing sized for fabricating catheters. All formulations were extruded into tubing of same cross-section. Samples of the same length and of each extruded polymer formulation were tested for dynamic torque properties at about 25° C. and at 37° C. The torque values were obtained on a Rheometrics RDS II Fluids Rheometer. The samples were subjected to either a 0.32 Hz or a 1.6 Hz frequency and a constant temperature. Dynamic torque values were obtained at about 18° rotation and about 27° rotation for 25° C. and 37° C.

Table II details the formulations used to prepare the tubing samples. Table III provides the torque values obtained at 18° rotation and at 27° rotation for both test temperatures. These values are presented for purposes of comparing different samples and different temperatures, it being recognized that different instruments and different operating techniques can result in variations in the results. Also, different tube cross-sections and/or lengths will exhibit different torque values.

TABLE II

| SAMPLE | 1 | 2 | 3 | 4 | 5 | 6 | 7 |
|---|---|---|---|---|---|---|---|
| Pellethane 2363-65D | 0 | 0 | 47.5 | 52.6 | 55.9 | 0 | 0 |
| Pellethane 2363-75D | 16 | 9.5 | 8.4 | 3.3 | 0 | 0 | 0 |
| Pellethane 2363-80A | 12.9 | 12.9 | 12.9 | 12.9 | 12.9 | 0 | 0 |
| Hytrel 5526 | 39.9 | 46.4 | 0 | 0 | 0 | 0 | 0 |
| BaSO4 | 30 | 30 | 30 | 30 | 30 | 30 | 30 |
| TiO2 and pigment | 1.2 | 1.2 | 1.2 | 1.2 | 1.2 | 0 | 0 |
| Vythene (PVC/Urethane Blend) | 0 | 0 | 0 | 0 | 0 | 70 | 0 |
| Plasticized PVC | 0 | 0 | 0 | 0 | 0 | 0 | 70 |

TABLE III

| Sample | Torque in gm-cm 18° rotation | | 27° rotation | |
|---|---|---|---|---|
| | 25° C. | 37° C. | 25° C. | 37° C. |
| 1 | 19.0 | 10.2 | 27 | 15.2 |
| 2 | 16.4 | 9.8 | 23.4 | 14.5 |
| 3 | 20.9 | 10.0 | 31.3 | 14.6 |
| 4 | 19.4 | 6.4 | 27.8 | 9.7 |

TABLE III-continued

| Sample | Torque in gm-cm | | | |
|---|---|---|---|---|
| | 18° rotation | | 27° rotation | |
| | 25° C. | 37° C. | 25° C. | 37° C. |
| 5 | 18.3 | 6.4 | 26.2 | 9.7 |
| 6 | 26.0 | 5.0 | 35.2 | 7.2 |
| 7 | 19.9 | 7.2 | 26.2 | 9.6 |

The data detailed in Table III quantitatively illustrate the large decreases in torque exhibited by tubing fabricated from all polyetherurethane and polyurethane/PVC blend. All polyurethane and the urethane/PVC blend samples 3–6 have good torque properties at room temperature, but have as much as an 80% drop in torque at physiological temperatures. Contrasted with these are Samples 1 and 2 which are exemplary polyetherurethane and polyetherester blends of the present invention. At room temperature, these samples have torque properties very close to prior art polymer formulations (Sample 7) and at 37° the blends of the present invention exhibit significantly lower decreases in torque. Also, while formulation 3 shows good absolute torque values, it is 100% polyetherurethane and more moisture sensitive for processing purposes than formulations that contain the polyetherester copolymer. And, its rebound properties are not as desirable as the polyetherurethane/polyetherester blends.

EXAMPLE 2

A preferred polymer blend of the present invention was prepared in accordance with the present invention and extruded to form catheter body tubing. The preferred polymer blend identified as PEU/PEE has the following formulation:

| PELLETHANE 2363-65D | 45.0 w/w % |
|---|---|
| PELLETHANE 2363-75D | 7.2 w/w % |
| PELLETHANE 2363-80A | 12.4 w/w % |
| HYTREL 5526 | 6.4 w/w % |
| BaSO$_4$ | 28.0 w/w % |
| TiO$_2$ | 1.0 w/w % |

The extruded tubing was tested for torque properties as described above for the samples in Example 1. Also tested for comparison were three pieces of tubing from commercially available catheters. The torque results at body temperature are detailed in Table IV below.

TABLE IV

| Sample | Torque in gm-cm | |
|---|---|---|
| | 15½ rotation 37½ C | 25½ rotation 37½ C |
| PVC 1 with reinforcement | 6.8 | 10.6 |
| PVC 2 | 5.3 | 8.2 |
| PVC 3 | 3.7 | 5.7 |
| PEU/PEE | 6.5 | 10.6 |

The data presented in Table IV illustrate that the polymer blend of the present invention (PEU/PEE) has superior 37½ C torque values when compared to commercially available polyvinylchloride (PVC) catheter materials. Moreover, the PEU/PEE polymer blend is comparable to PVC materials incorporating reinforcement for the purpose of improving torque properties. Thus, in addition to providing highly desirable polymers in the form of polyetherurethanes, the polymer blends of the present invention exhibit superior performance relative to prior art materials.

EXAMPLE 3

Certain physical properties such as bend stiffness are important considerations in the materials of the present invention. For example, the materials should not be so stiff that catheters fabricated from them are likely to perforate tissue during their use. On the other hand, the materials should be stiff enough, especially at ambient temperature, to pass through introducers without buckling. In order to determine the relative stiffness of several catheters and their respective formulations, and specifically of PVC 1 reinforced, PVC 3, and PEU/PEE described in Example 2, bend stiffness tests were performed on these samples. The bend stiffness test measures the amount of force required to deflect a given length of catheter body 1.2 mm. Table V gives the bend stiffness data for each of the samples.

TABLE V

| Sample | Bend Stiffness (gm) | |
|---|---|---|
| | 25° C. | 37° C. |
| PVC 1 reinforced | 11.7 | 3.2 |
| PVC 3 | 3.9 | 1.5 |
| PEU/PEE | 3.5 | 1.6 |

These results indicate that catheter tubes made from the polymer blends of the present invention exhibit comparable bend stiffness performance to commercial PVC catheters. Furthermore, the bend stiffness values are on the low side, which means lower perforation potential.

EXAMPLE 4

A comparative study of the performance of a catheter fabricated from a polymer blend of the present invention versus commercial catheters was performed. The study was carried out in male sheep and characterized the ease of floatation, the maneuvering properties, and the right heart placement of two PVC catheters and of catheters formed of the PEU/PEE polymer blend identified in Example 2.

The catheters were inserted through an 8F introducer and floated into the pulmonary artery with a balloon inflation of 1 to 1.5 cc. Fluoroscopy was utilized to visualize the catheters. Results of the animal studies indicated that catheters fabricated of PEU/PEE were substantially easier to insert into the introducer. The overall performance rating with respect to maneuverably indicated that the polymer blends of the present invention exhibit a relative greater maneuverability when compared to commercially available catheters.

EXAMPLE 5

A comparative study of the performance of two catheters fabricated from a polymer blend of the present invention versus the performance of commercial catheters was performed. The study was carried out in male sheep and characterized the catheter handling near the introducer in terms of its column strength and ease with which the catheter is fed through the introducer without buckling. The test was performed by feeding the catheter through the introducer, without buckling, and then moving the introducing fingers incrementally and proximally away from the introducer until the maximum distance at which the catheter was capable of being fed without buckling was reached. Table VI details the results of this study for 3 commercial polyvinylchloride catheters and two catheters prepared from the polymer blend of the present invention.

TABLE VI

| Distance From Introducer At Which Catheter Was Capable of Being Fed Without Buckling | |
|---|---|
| Catheter Polymer | Distance (cm) |
| PVC A | 4.5 |
| PVC B | 6.0 |
| PEU/PEE | 5.8 |
| PVC C | 7.0 |

The results illustrate the very favorable column strength and resistance to buckling associated with the catheters prepared from the PEU/PEE blends of the present invention.

EXAMPLE 6

A number of dogbone shaped samples of the PEU/PEE polymer blend identified in Example 2 were prepared and sterilized with up to 3 standard ethylene oxide sterilization cycles. After each cycle a number of dogbones were tested for any loss in tensile strength which may have resulted from the sterilizing process. One set of samples was aged for a total of 10 days under accelerated aging conditions —1 day at 65° C. and 80% relative humidity, 6 days at 65° C, and 3 days at 65° C. and 80% relative humidity. The results are illustrated in Table VI.

TABLE VI

| No. ETO cycles | Mean force/area at break (PSI) | No. of Samples |
|---|---|---|
| 0 | 4136 | 4 |
| 1 | 4018 | 4 |
| 1 + aging | 3675 | 5 |
| 3 | 4201 | 4 |

These results indicate that sterilization has little effect on the tensile strength of the material at break. While accelerated aging may have weakened the material about 10%, this is not a problem considering the strength of the material.

Having thus described exemplary embodiments of the present invention, it should be noted by those skilled in the art that the disclosures herein are exemplary only and that alternatives, adaptations and modifications may be made within the scope of the present invention.

We claim:

1. A catheter useful for accessing body cavities during therapeutic and diagnostic medical procedures, said catheter comprising:
    an elongated tubular member having at least one lumen, said elongated tubular member formed of a heat extruded homogeneous polymer blend of polyetherurethane and polyetherester, wherein said polymer blend provides the catheter with enhanced torque retention and balanced rebound properties.

2. The catheter of claim 1 wherein said polyetherester is present in said polymer blend at a concentration of at least 5 w/w%.

3. The catheter of claim 1 wherein said polyetherurethane further includes a first polyetherurethane having a Shore hardness of about 65 D at 25° C., a second polyetherurethane having a Shore hardness of about 75 D at 25° C., and a third polyetherurethane having a Shore hardness of about 80 A at 25° C.

4. The catheter of claim 3 wherein said polymer blend includes from 0 w/w% to about 65 w/w% of said first polyetherurethane, from about 5 w/w% to about 35 w/w% of said second polyetherurethane, and from 0 w/w% to about 15 w/w% of said third polyetherurethane.

5. The catheter of claim 1 wherein said polymer blend further includes a filler of radiopaque material.

6. The catheter of claim 1 wherein said polymer blend further includes additives selected from the group consisting of TiO$_2$ and pigments.

7. The catheter of claim 1 wherein said polymer blend includes about 45 w/w% polyetherurethane having a Shore hardness of 65 D, about 7.2 w/w% polyetherurethane having a Shore hardness of 75 D, about 12.4 w/w% polyetherurethane having a Shore hardness of 80 A, about 6.4 w/w% polyetherester, about 1% TiO$_2$, and about 28 w/w% BaSO$_4$ radiopaque material.

8. The catheter of claim 1 wherein said polymer blend includes inorganic compounds selected from the group consisting of radiopaque filler and pigments.

9. The composition of claim 8 wherein said radiopaque filler is BaSO$_4$.

10. The catheter of claim 1 wherein said polyetherester is present in said polymer blend at a concentration of from about 5 w/w% to about 45 w/w%.

11. The catheter of claim 1 wherein said polymer blend includes from about 25 w/w% to about 75 w/w% polyetherurethane, from about 5 w/w% to about 45 w/w% polyetherester, from about 15 w/w% to about 30 w/w% filler of radiopaque material, and about 1 w/w% pigment.

12. A catheter having improved maneuverability and torque transmitting properties at 25° C. and 37° C., said catheter comprising:
    an elongated tubular member having at least one lumen, said elongated tubular member formed of a thermoplastic homogenous blend of polyetherurethane and polyetherester, said blend having from about 5 w/w% to about 45 w/w% polyetherester, from about 0 w/w% to about 45 w/w% polyetherurethane having a Shore hardness of 65 D, from about 7.2 w/w% to about 16 w/w% polyetherurethane having a Shore hardness of 75 D, and from about 12.4 w/w% to about 12.9 w/w% polyetherurethane having a Shore hardness of 80 A or 40 D.

13. The catheter of claim 1 wherein said polymer blend further includes inorganic compounds selected from the group consisting of radiopaque filler and pigments.

14. The catheter of claim 1 wherein said polyetherurethane is present in said polymer blend at a concentration of at least 22.4 w/w%.

15. The catheter of claim 1 wherein said polyetherurethane is present in said polymer blend at a concentration of from about 25 w/w% to about 75 w/w%.

16. The catheter of claim 1 wherein said polyetherester has a Shore hardness of about 55 D at 25° C.

17. The catheter of claim 5 wherein said radiopaque filler is BaSO$_4$.

18. The catheter of claim 1 wherein said polymer blend includes about 16.0 w/w% polyetherurethane having a Shore hardness of 75 D, about 12.9 w/w% polyetherurethane having a Shore hardness of 80 A, about 39.9 w/w% polyetherester having a hardness of about 55 D, about 0.8% TiO$_2$, about 30 w/w% BaSO$_4$ radiopaque material, and about 0.4% pigment.

19. The catheter of claim 1 wherein said polymer blend includes about 9.5 w/w% polyetherurethane having a Shore hardness of 75 D, about 12.9 w/w% polyetherurethane having a Shore hardness of 80 A, about 46.4 w/w% polyetherester having a hardness of about 55 D, about 0.8% TiO$_2$, about 30 w/w% BaSO$_4$ radiopaque material, and about 0.4% pigment.

20. A catheter useful for accessing body cavities during therapeutic and diagnostic medical procedures, said catheter comprising:

an elongated tubular member having at least one lumen, said elongated tubular member formed of a heat extruded homogeneous polymer blend of polyetherurethanes and polyetherester, said blend having about 45 w/w% polyetherurethane having a Shore hardness of 65 D, about 7.2 w/w% polyetherurethane having a Shore hardness of 75 D, about 12.4 w/w% polyetherurethane having a Shore hardness of 80 A, about 6.4 w/w% polyetherester having a hardness of about 55 D, about 1% TiO$_2$, and about 28 w/w% BaSO$_4$ radiopaque material.

21. A catheter useful for accessing body cavities during therapeutic and diagnostic medical procedures, said catheter comprising:

an elongated tubular member having at least one lumen, said elongated tubular member formed of a heat extruded homogeneous polymer blend of polyetherurethanes and polyetherester, said blend having about 16 w/w% polyetherurethane having a Shore hardness of 75 D, about 12.9 w/w% polyetherurethane having a Shore hardness of 80 A, about 39.9 w/w% polyetherester having a hardness of about 55 D, about 1.2% TiO$_2$, and about 30 w/w% BaSO$_4$ radiopaque material.

22. A catheter useful for accessing body cavities during therapeutic and diagnostic medical procedures, said catheter comprising:

an elongated tubular member having at least one lumen, said elongated tubular member formed of a heat extruded homogeneous polymer blend of polyetherurethanes and polyetherester, said blend having about 9.5 w/w% polyetherurethane having a Shore hardness of 75 D, about 12.9 w/w% polyetherurethane having a Shore hardness of 80 A, about 46.4 w/w% polyetherester having a hardness of about 55 D, about 1.2% TiO$_2$, and about 30 w/w% BaSO$_4$ radiopaque material.

* * * * *